United States Patent [19]

Franke et al.

[11] Patent Number: 4,714,710
[45] Date of Patent: Dec. 22, 1987

[54] INSECTICIDAL AND ACARICIDAL OXETANE AND THIETANE DERIVATIVES, COMPOSITIONS, AND METHOD OF USE THEREFOR

[75] Inventors: Heinrich Franke; Hartmut Joppien; Helga Franke, all of Berlin, Fed. Rep. of Germany

[73] Assignee: Schering Aktiengesellschaft, Fed. Rep. of Germany

[21] Appl. No.: 905,275

[22] Filed: Sep. 9, 1986

[30] Foreign Application Priority Data

Sep. 9, 1985 [DE] Fed. Rep. of Germany ....... 3532478

[51] Int. Cl.$^4$ .................. A01N 43/20; A61K 31/335; A61K 31/38; C07D 305/06
[52] U.S. Cl. .................................... 514/430; 514/336; 514/438; 514/444; 514/449; 514/461; 514/464; 514/465; 549/88; 549/435; 549/451; 549/453; 549/510; 549/511; 546/283; 546/284
[58] Field of Search ............... 549/88, 435, 451, 453, 549/510, 511, 336; 514/438, 444, 461, 464, 465, 430, 449; 546/383, 384

[56] References Cited

U.S. PATENT DOCUMENTS 4,570,005 2/1986 Nakatani et al. ..................... 549/435

OTHER PUBLICATIONS

JP Abstract, Sumitomo Chem. Ind. KK, JP 146661, 2/3/86.

Primary Examiner—Henry R. Jiles
Assistant Examiner—J. G. Mullins
Attorney, Agent, or Firm—Ostrolenk, Faber, Gerb & Soffen

[57] ABSTRACT

There are described new compounds of general formula I

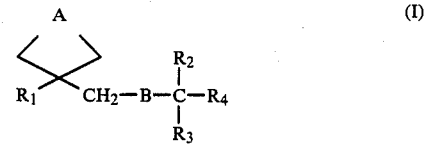

in which $R_1$ is aryl or aryl substituted by $C_{1-4}$-alkyl, halo-$C_{1-4}$-alkyl, phenyl-$C_{1-4}$-alkyl, $C_{2-4}$-alkenyl, halo-$C_{2-4}$-alkenyl, phenyl-$C_{2-4}$-alkenyl, $C_{2-4}$-alkynyl, halo-$C_{2-4}$-alkynyl, phenyl-$C_{2-4}$-alkynyl, $C_{1-4}$-alkoxy, halo-$C_{1-4}$-alkoxy, phenyl-$C_{1-4}$-alkoxy, $C_{2-4}$-alkenyloxy, alkylsulphonyloxy, haloalkylsulphonyloxy, arylsulphonyloxy, halo-$C_{2-4}$-alkenyloxy, phenyl-$C_{2-4}$-alkenyloxy, halo, cyano, nitro, aryloxy, haloaryloxy, $C_{1-4}$-alkylaryloxy, or nitro-$C_{1-4}$-alkylaryloxy, $R_2$ and $R_3$ are the same or different and are hydrogen, fluorine, cyano or ethynyl, $R_4$ is phenyl or pyridyl or these groups substituted by one or more of $C_{1-6}$-alkyl, halo-$C_{1-6}$-alkyl, phenyl-$C_{1-6}$-alkyl, $C_{1-6}$-alkyl interrupted by an O—, N— or S— atom, $C_{2-4}$-alkenyl, halo-$C_{2-4}$-alkenyl, phenyl-$C_{2-4}$-alkenyl, $C_{1-4}$-alkoxy, halo-$C_{1-4}$-alkoxy, phenyl-$C_{1-4}$-alkoxy, $C_{2-4}$-alkenyloxy, halo-$C_{2-4}$-alkenyloxy, phenyl-$C_{2-4}$-alkenyloxy, aryloxy, haloaryloxy, $C_{1-4}$-alkylaryloxy, arylamino, haloarylamino, $C_{1-4}$-alkylarylamino, aryl-N—$C_{1-4}$-alkylamino, aryl-N—$C_{1-4}$ acylamino, aroyl, haloaroyl, $C_{1-4}$-alkylaroyl, aryl, haloaryl, $C_{1-4}$-alkylaryl or halo, A is O or S and
B is $CH_2$ or O, processes for their preparation and their use as insecticides and acaricides.

18 Claims, No Drawings

INSECTICIDAL AND ACARICIDAL OXETANE AND THIETANE DERIVATIVES, COMPOSITIONS, AND METHOD OF USE THEREFOR

This invention relates to oxetane and thietane derivatives and their preparation, as well as pesticidal compositions based on these compounds.

Synthetic pyrethroids are a well known group of inseticides. In recent years there have been described pyrethroids in which the conventional ester grouping has been replaced by an ether or alkylene chain as for example in EP No. 94,085, EP No. 104,908 and DE No. 3,317,908. We are not aware however of compounds of this type containing an oxetane or thietane group in the main chain.

It has now been found that compounds according to the invention possess particularly valuable insecticidal and acaricidal properties. The compounds are of general formula I

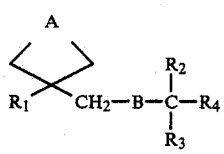

in which
R$_1$ is aryl or aryl substituted by C$_{1-4}$-alkyl, halo-C$_{1-4}$-alkyl, phenyl-C$_{1-4}$-alkyl, C$_{2-4}$-alkenyl, halo-C$_{2-4}$-alkenyl, phenyl-C$_{2-4}$-alkenyl, C$_{2-4}$-alkynyl, halo-C$_{2-4}$-alkynyl, phenyl-C$_{2-4}$-alkynyl, C$_{1-4}$-alkoxy, halo-C$_{1-4}$-alkoxy, phenyl-C$_{1-4}$-alkoxy, C$_{2-4}$-alkenyloxy, alkylsulphonyloxy, haloalkylsulphonyloxy, arylsulphonyloxy, halo-C$_{2-4}$-alkenyloxy, phenyl-C$_{2-4}$-alkenyloxy, halo, cyano, nitro, aryloxy, haloaryloxy, C$_{1-4}$-alkylaryloxy, or nitro-C$_{1-4}$-alkylaryloxy, R$_2$ and R$_3$ are the same or different and are hydrogen, fluorine, cyano or ethynyl, R$_4$ is phenyl or pyridyl or these groups substituted by one or more of C$_{1-6}$-alkyl, halo-C$_{1-6}$-alkyl, phenyl-C$_{1-6}$-alkyl, C$_{1-6}$-alkyl interrupted by an O—, N— or S— atom, C$_{2-4}$-alkenyl, halo-C$_{2-4}$-alkenyl, phenyl-C$_{2-4}$-alkenyl, C$_{1-4}$-alkoxy, halo-C$_{1-4}$-alkoxy, phenyl-C$_{1-4}$-alkoxy, C$_{2-4}$-alkenyloxy, halo-C$_{2-4}$-alkenyloxy, phenyl-C$_{2-4}$-alkenyloxy, aryloxy, haloaryloxy, C$_{1-4}$-alkylaryloxy, arylamino, haloarylamino, C$_{1-4}$-alkylarylamino, aryl-N—C$_{1-4}$-alkylamino, aryl-N—C$_{1-4}$ acylamino, aroyl, haloaroyl, C$_{1-4}$-alkylaroyl, aryl, haloaryl, C$_{1-4}$-alkylaryl or halo, A is O or S and
B is CH$_2$ or O.

The aryl group designated as R$_1$ in general formula I also includes 1-naphthyl, 2-naphthyl, benzofuran-5-yl, benzothiophen-5-yl, benzofuran-6-yl, benzothiophen-6-yl, benzoxazol-5-yl, benzoxazol-6-yl, indan-5-yl, indan-6-yl, 1,4-benzodioxan-6-yl, 1,3-benzodioxan-6-yl, 1,3-benzodioxan-7-yl and 1,3-benzodioxol-5-yl.

A particularly preferred group of compounds is that in which R$_2$ and R$_3$ are both hydrogen and R$_4$ is 3-phenoxyphenol or 4-fluoro-3-phenoxyphenyl. A is preferably O and B is preferably CH$_2$. R$_1$ is preferably phenyl, optionally substituted in the 4-position or in both the 3- and 4-positions by halogen, C$_{1-4}$-alkyl, C$_{1-4}$-alkoxy, C$_{1-4}$-haloalkyl or C$_{1-4}$-haloalkoxy or two adjacent substituents form a methylenedioxy group. Particularly preferred substituents are halogen (especially chloride and fluorine), methyl, trifluoromethyl and ethoxy.

The oxetanes of the invention of formula I in which A is oxygen can be prepared by treating a compound of formula II

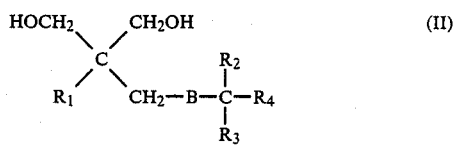

firstly with a sulphonyl chloride to give a compound of formula III

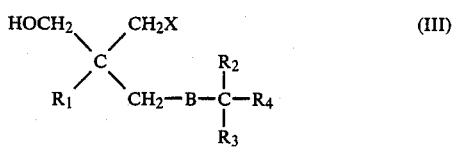

in which R$_1$, R$_2$, R$_3$, R$_4$ and B have the meanings given above and X is a leaving group, such as halogen, mesylate or tosylate, and then cyclising this to the oxetane, with a strong base.

The cyclisation reaction is generally carried out in solution. Suitable bases are metal alcoholates, such as for example potassium tert.-butylate, metal hydrides, such as for example sodium hydride, metal amides, such as for example lithium diisopropylamide and metal alkyl compounds, such as for example ethyl magnesium bromide or butyl lithium.

Suitable solvents, as opposed to the reactants, especially the bases, include inert substances such as aliphatic and aromatic hydrocarbons such as for example hexane, benzene or toluene and ethers such as for example diethyl ether, tetrahydrofuran or dimethoxyethane. Further, amides, such as for example dimethylformamide and diethylformamide may be suitable.

The reaction is carried out at a temperature of −78° to 140° C., preferably at 20°–80° C. and usually at atmospheric pressure.

It is particularly advantageous to carry out both reaction stages in a so-called one-pot reaction as is described in "P. Picard, D. Leclercq, J.-P. Bats, J. Moulines, Synthesis 550 (1981)".

The thietanes of the invention of formula I in which A is sulphur can be prepared by treating a compound of formula II with a sulphonyl chloride to give an intermediate of general formula IV

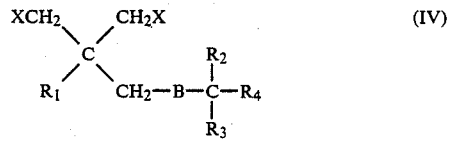

in which R$_1$, R$_2$, R$_3$, R$_4$, X and B have the meanings given above and then cyclising this to the thietane with sodium sulphide.

The cyclisation reaction is generally carried out in solution. It is especially advantageous to use dimethyl sulphoxide as solvent and a reaction temperature of 80°–100° C.

The diols used as starting materials can be prepared in a two stage synthesis in which a substituted malonate ester of the general formula

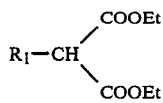

is reacted with an alkylating agent of general formula

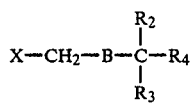

in which $R_1$, $R_2$, $R_3$, $R_4$, X and B have the meanings given above, in the presence of a base and then the disubstituted malonate ester is reduced to the diol with lithium aluminium hydride.

The compounds of the invention obtained by these processes may be isolated in conventional manner for example by distillation of the solvent at normal or reduced pressures, by precipitation with water or by extraction.

A high degree of purity can be achieved as a general rule by column chromatography as well as by fractional distillation or crystallisation.

The compounds are colourless and odourless oils that dissolve well in practically all organic solvents but are almost insoluble in water.

The compounds of the invention have insecticidal and acaricidal activity and are particularly useful in combating a variety of economically important insects, and acarids including animal ectoparasites. Examples include Lepidoptera, such as *Plutella xylostella*, *Spodoptera littoralis*, *Heliothis armigera*, and *Pieris brassicae*; Diptera, such as *Musca domestica, ceratitis capitata, Erioischia brassicae, Lucilia sericata* and *Aedes aegypti;* Homoptera, including aphids such as *Megoura viciae* and *Nilaparvata lugens;* Coleoptera, such as *Phaedon cochleariae, Anthonomus grandis* and *Epilachna varivestis* and corn rootworms (Diabrotica spp., e.g. *Diabrotica undecimpunctata*); Orthoptera, such as cockroaches e.g. *Blattella germanica;* Hymenoptera, such as ants e.g. *Monomorium pharaonis;* mange mites, e.g. Sarcoptes spp.; ticks, such as *Boophilus microplus* and lice, such as *Damalinia bovis* and *Linognathus vituli;* as well as spider mites such as *Tetranychus urticae* and *Panonychus ulmi.*

The compounds are distinguished by a surprisingly high level of activity against important pest species, especially ticks, which is greater than that of known pesticidal compositions having a similar mode of action.

The compounds according to the invention can be used at a concentration of 0.0005 to 5%, preferably from 0.001 to 1%, calculated as gram active material per 100 ml of the composition.

The compounds of the invention can be used either alone or in mixture with each other or another insecticide. Optionally other plant protection or pesticidal compositions, such as for example insecticides, acaricides or fungicides can be added depending on the desired result.

An improvement in the intensity and speed of action can be obtained, for example, by addition of suitable adjuvants, such as organic solvents, wetting agents and oils. Such additives may allow a decrease in the dose.

Suitable mixture partners may include phospholipids, e.g. phosphatidylcholine, hydrated phosphatidylcholines, phosphatidylethanolamine, N-acyl-phosphatidylethanolamines, phosphatidylinositol, phosphatidylserine, lysolecithin or phosphatidylglycerol.

The designated active ingredients or their mixtures can suitably be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example, water, aliphatic and aromatic hydrocarbons such as benzene, toluene, xylene, cyclohexanone, isophorone, dimethyl sulphoxide, dimethylformamide, other mineral-oil fractions and plant oils.

Suitable solid carriers include mineral earths, e.g. bentonite, silica gel, talcum, kaolin, attapulgite, limestone, silicic acid and plant products, e.g. flours.

As surface-active agents, there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts.

The percentage of the active ingredient(s) in the various preparations can vary within wide limits. For example, the compositions can contain about 10 to 90 percent by weight active ingredients, and about 90 to 10 percent by weight liquid or solid carriers, as well as, optionally up to 20 percent by weight of surfactant.

The agents can be applied in customary fashion, for example with water as the carrier in spray mixture volumes of approximately 100 to 3,000 l/ha. The agents can be applied using low-volume or ultra-low-volume techniques or in the form of so-called microgranules.

The preparation of these formulations can be carried out in a known manner, for example by milling or mixing processes. Optionally, individual components can be mixed just before use for example by the so-called commonly used tank-mixing method.

Formulations can be prepared, for example, from the following ingredients.

| | |
|---|---|
| (a) | 80 percent by weight active ingredient |
| | 15 percent by weight kaolin |
| | 5 percent by weight surface-active agent based on the sodium salt of N—methyl-N—oleyltaurine and the calcium lignosulphonate |
| (b) | 45 percent by weight active ingredient |
| | 5 percent by weight sodium aluminium silicate |
| | 15 percent by weight cetylpolyglycol ether with 8 moles ethylene oxide |
| | 2 percent by weight spindle oil |
| | 10 percent by weight polyethylene glycol |
| | 23 parts water |
| (c) | 20 percent by weight active ingredient |
| | 35 percent by welqht bentonite |
| | 8 percent by weight calcium lignosulphonate |
| | 2 percent by weight of the sodium salt of N—methyl-N—oleyltaurine |
| | 35 percent by weight silicic acid |
| (d) | 20 percent by weight active ingredient |
| | 75 percent by weight isophorone |
| | 5 percent by weight of an emulsifier mixture of calcium phenylsulphonate and fatty alcohol polyglycol ether |

The following examples illustrate the preparation of compounds acording to the invention.

EXAMPLE 1

3-(4-Ethoxyphenyl)-3-[3-(3-phenoxyphenyl)propyl]oxetane

A solution of butyl lithium in n-hexane (4.7 ml, 1.6M) was added dropwise at 0° C. to 2-(4-ethoxyphenyl)-2-[3-(3-phenoxyphenyl)propyl]propane-1,3-diol (2.8 g), dissolved in tetrahydrofuran (THF) (15 ml). After 10 minutes, p-toluenesulphonyl chloride (1.3 g) dissolved in THF (10 ml) was added dropwise at 0° C. and after another 45 minutes, more butyl lithium solution in n-hexane (4.7 ml, 1.6M) was added. After stirring for one hour at 0° C. and 12 hours at room temperature, the mixture was added to ice-water, extracted three times with ether, the extract washed with water, dried over magnesium sulphate and evaporated. After chromatography on silica-gel using ether/hexane (1:9) as eluent, there was obtained 1.6 g of product (60% of theory). $n_D^{20}$: 1.5784

Preparation of starting material

Sodium hydride (6.2 g of a 55% dispersion) was washed free of oil with toluene and then treated with dimethyl sulphoxide (300 ml), sodium iodide (5.5 g) and 1-bromo-3-(3-phenoxyphenyl)propane (36.4 g; 125 mmol). Diethyl 4-ethoxyphenylmalonate (40 g, 143 mmol) was added, dropwise, at room temperature and then stirred for twenty hours at this temperature. The mixture was added to ice-water, extracted three times with ether, the extracts washed with water, dried over magnesium sulphate and evaporated. After chromatography on silica-gel, there was obtained 53.4 g of diethyl 2-(4-ethoxyphenyl)-2-[3-phenoxyphenyl)-propyl]malonate (87% of theory). $n_D^{20}$: 1.5456.

A solution of this product (25 g, 51 mmol) in ether (170 ml) was added dropwise to lithium aluminium hydride (3.9 g, 102 mmol) in ether (170 ml). The mixture was heated under reflux for one hour and then carefully hydrolysed, first with water and then 10% sulphuric acid. It was then extracted three times with ethyl acetate, the extract washed with water, dried over magnesium sulphate and evaporated to give 19.8 g of 2-(4-ethoxyphenyl)-2-[3-(3-phenoxyphenyl)propyl]propane-1,3-diol. $n_D^{20}$: 1.5860

EXAMPLE 2

3-(4-Ethoxyphenyl)-3-[3-(3-phenoxyphenyl)propyl]thietane 2-(4-Ethoxyphenyl)-2-[3-(3-phenoxyphenyl)propyl]propane-1,3-diol ditosylate (39.5 g) and sodium sulphide (Na$_2$S.9H$_2$O; 13.3 g) were stirred in dimethyl sulphoxide (300 ml) at 90° C. for 3 hours. The mixture was then poured into ice-water, extracted with ether, dried and evaporated. The crude product was purified by silica gel chromatography to give 17.0 g of product as a colourless oil (76% of theory). $n_D^{20}$: 1.5976.

Preparation of the starting material 2-(4-Ethoxyphenyl)-2-[3-(3-phenoxyphenyl)propyl]propane-1,3-diol (25 g) was dissolved in pyridine (150 ml) and 4-dimethylaminopyridine added (20 mg). p-Toluenesulphonyl chloride (23.4 g), dissolved in pyridine (20 ml), was added dropwise at −5° C. The mixture was allowed to rise to room temperature over 2 hours and stirred overnight. It was then added to a hydrochloric acid-ice mixture, extracted with ether and the extract dried and evaporated to give 40.1 g of crude product which was used without further purification.

EXAMPLE 3

3-(4-Ethoxyphenyl)-3-(4-fluoro-3-phenoxybenzyloxymethyl)-oxetane p In a similar manner to Example 1, starting from 2-(4-ethoxyphenyl)-2-(4-fluoro-3-phenoxybenzyloxymethyl)propane-1,3-diol, there was obtained the title compound as an oil, $n_D^{20}$: 1.5699

Preparation of starting material

Sodium (2.18 g, 35 mmol) was added to diethyl 4-ethoxyphenylmalonate (26.6 g, 95 mmol) dissolved in dioxane (100 ml) and refluxed until the sodium had dissolved. Chloromethyl(4-fluoro-3-phenoxybenzyl)ether (25.4 g, 95 mmol) was added, dropwise, at 40°–50° C. and then heated under reflux for 3 hours. The mixture was added to ice-water, extracted three times with ether, the extracts washed with water, dried over magnesium sulphate and evaporated. After chromatography on silica-gel, using toluene as the eluent, there was obtained 25.3 g of diethyl 2-(4-ethoxyphenyl)-2-(4-fluoro-3-phenoxybenzyloxymethyl)malonate (52% of theory). This was then reduced in a similar manner to Example 1 using lithium aluminium hydride to give crude 2-(4-ethoxyphenyl)-2-(4-fluoro-3-phenoxybenzyloxymethyl)propane-1,3-diol.

In a similar manner the following compounds according to the invention were prepared.

| Example No. | Compound | Physical constant $n_D^{20}$ or mp. |
|---|---|---|
| 4 | 3-[3-(3-phenoxyphenyl)propyl]-3-phenyloxetane | 1.5838 |
| 5 | 3-(4-chlorophenyl)-3-[3-(3-phenoxyphenyl)propyl]oxetane | 1.5884 |
| 6 | 3-(3,4-dimethoxyphenyl)-3-[3-(3-phenoxyphenyl)propyl]oxetane | 1.5824 |
| 7 | 3-(4-chlorophenyl)-3-(3-phenoxybenzyloxymethyl)oxetane | 1.5840 |
| 8 | 3-(4-ethoxyphenyl)-3-(3-phenoxybenzyloxymethyl)oxetane | 1.5798 |
| 9 | 3-(4-methoxyphenyl)-3-[3-(3-phenoxyphenyl)propyl]oxetane | 1.5867 |
| 10 | 3-(4-ethoxyphenyl)-3-[3-(4-fluoro-3-phenoxyphenyl)propyl]oxetane | 1.5673 |
| 11 | 3-(4-chlorophenyl)-3-[3-(4-fluoro-3-phenoxyphenyl)propyl]oxetane | 1.5760 |
| 12 | 3-(4-chlorophenyl)-3-(4-fluoro-3-phenoxybenzyloxymethyl)oxetane | 78–80° C. |
| 13 | 3-(4-chlorophenyl)-3-[3-(3-phenoxyphenyl)propyl]thietane | 1.6137 |
| 14 | 3-(4-chlorophenyl)-3-(3-phenoxybenzyloxymethyl)thietane | 1.6082 |
| 15 | 3-(4-ethoxyphenyl)-3-(3-phenoxybenzyloxymethyl)thietane | 1.6000 |
| 16 | 3-[3-(3-phenoxyphenyl)propyl]-3-phenylthietane | 1.6121 |
| 17 | 3-(3,4-dimethoxyphenyl)-3-[3-(3-phenoxyphenyl)propyl]thietane | 1.6046 |
| 18 | 3-(4-ethoxyphenyl)-3-[3-(4-fluoro-3-phenoxyphenyl)propyl]thietane | 1.5901 |
| 19 | 3-(4-methoxyphenyl)-3-[3-(3-phenoxyphenyl)propyl]thietane | 1.6055 |
| 20 | 3-(4-chlorophenyl)-3-[3-(4-fluoro-3-phenoxyphenyl)propyl]thietane | 1.6053 |
| 21 | 3-(4-fluorophenyl)-3-[3-(3-phenoxyphenyl)propyl]oxetane | 1.5761 |
| 22 | 3-(4-methylphenyl)-3-[3-(3-phenoxyphenyl)propyl]oxetane | 1.5834 |
| 23 | 3-[3-(3-phenoxyphenyl)propyl]-3-(4-trifluoromethylphenyl)oxetane | 1.5503 |
| 24 | 3-[4-(2-fluoroethoxy)phenyl)-3-[3-(3-phenoxyphenyl)propyl]oxetane | 1.5767 |
| 25 | 3-[3-(3-phenoxyphenyl)propyl]-3- | 1.5748 |

| Example No. | Compound | Physical constant $n_D^{20}$ or mp. |
|---|---|---|
| | (4-propoxyphenyl)oxetane | |
| 26 | 3-[4-(1-methylethoxy)phenyl]-3-[3-(3-phenoxyphenyl)propyl]oxetane | 1.5715 |
| 27 | 3-(3,4-methylenedioxy)phenyl)-3-[3-(3-phenoxyphenyl)propyl]oxetane | 1.5923 |
| 28 | 3-(4-ethoxy-3-fluoro)phenyl)-3-[3-(3-phenoxyphenyl)propyl]oxetane | 1.5713 |

The following Examples illustrate the possible uses of the compounds of the invention, that are in the form of the previously mentioned preparations.

EXAMPLE 29

Activity against larvae (L2) of the cotton army worm (*Spodoptera littoralis*)

Compounds of the invention were made up as aqueous emulsions at a concentration of 0.1%. Leaflet pairs of beans (*Vicia fabae*) as well as 10 larvae (L2) of the cotton army worm (*Spodoptera littoralis*) per experiment were sprayed with 4 mg spray/cm$^2$ of these preparations in polystyrene petri dishes. The closed petri dishes were left in the laboratory under extended daylight conditions for two days. The % mortality of the larvae after two days indicated the level of activity.

In these experiments, the compounds of Examples 1–28 caused 100% mortality.

EXAMPLE 30

Activity against larvae (L3) of the Mexican bean beetle (*Epilachna varivestis*)

Compounds were made up as aqueous emulsions at a concentration of 0.1%. French bean plants (*Phaseolus vulgaris*) in the primary leaf stage were dipped in the preparations. For each test, two plant stems with 4 primary leaves were placed in glass vases filled with water and enclosed in plexiglass cylinders. Then 5 larvae of the Mexican bean beetle (*Epilachna varivestis*) at the third larval stage were put in the glass cylinders and kept for 3 days. The % mortality of the larvae after 3 days indicated the level of activity.

In these experiments the compounds of Examples 1–28 caused 100% mortality.

EXAMPLE 31

Insecticidal and acaricidal activity against *Boophilus microplus* (1), *Lucilia sericata* (2) *Musca domestica* (3) and *Blattella germanica* (4).

1. 9 cm diameter filter papers where impregnated with 1 ml aliquots of acetone solutions of test compound at various concentrations. The papers were allowed to dry and then folded into envelopes in which cattle tick larvae, (*Boophilus microplus*) were enclosed and held at 25° C. and 80% R.H. for 48 hours. The percentage mortality of tick larvae was then recorded and compared with controls. The controls gave a mortality of less than 5% whereas compounds of Examples 1–7, 9–18 and 21–28 caused at least 50% mortality at a concentration of 300 ppm or less.

2. 1 ml aliquots of an acetone solution containing test compound at various concentrations were applied to cotton wool dental rolls 1 cm×2 cm, contained in glass vials (2 cm diameter×5 cm long). After drying, the treated materials were then impregnated with 1 ml of nutrient solution, infested with first instar larvae of sheep blowfly (*Lucilia sericata*), closed by a cotton wool plug and held at 25° C. for 24 hours. For the controls, the mortality was <5% whereas the compounds of Examples 1–13, 15, 17, 18 and 21–28 had an LC$_{50}$ of 300 ppm or less.

3. Aliquots of acetone solutions of test compounds at various concentrations were applied to 9 cm diameter filter papers placed in the bottom of 9 cm diameter petri dishes closed by glass lids. After evaporation of solvent, the treated surfaces, together with control treated with acetone alone, were then infested with adult houseflies, (*Musca domestica*) and held at 22° C. for 24 hours. The percentage mortality of the insects was then recorded. Less than 5% mortality resulted in the control treatments whereas the compounds of Examples 1, 5, 9, 10 and 22–28 had an LD$_{50}$ of 1000 mg/m$^2$ or less.

4. Aliquots of acetone solutions of test compounds at various concentrations were applied to glass plates (10 cm×10 cm). After evaporation of solvent, the treated surfaces, together with controls treated with acetone alone, were then infested with second instar nymphs of the German cockroach, (*Blattella germanica*), retained on the treated surface within PTFE-coated glass rings 6 cm in diameter and held for 24 hours at 22° C. The percentage mortality of the insects was then recorded.

Less than 5% mortality resulted in the control treatments whereas the compounds of Examples 1–13, 15, 18, 19, 21–23, 25, 27 and 28 had an LD$_{50}$ of 300 mg/m$^2$ or less.

We claim:

1. A compound of the formula

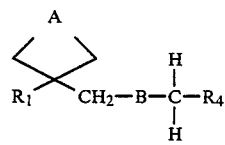

in which

R$_1$ is phenyl or phenyl substituted by C$_{1-4}$-alkyl, halo-C$_{1-4}$-alkyl, C$_{1-4}$-alkoxy, halo-C$_{1-4}$-alkoxy or methylenedioxy, R$_4$ is phenoxyphenyl or halophenoxyphenyl, A is O or S and B is CH$_2$ or O.

2. A compound according to claim 1 in which R$_4$ is 3-phenoxyphenyl or 4-fluoro-3-phenoxyphenyl.

3. A compound according to claim 2, in which A is O.

4. A compound according to claim 3, in which B is CH$_2$.

5. A compound according to claim 4, in which the R$_1$ is phenyl substituted in the 4-position or in both the 3- and 4-positions.

6. A compound according to claim 5, in which R$_1$ is phenyl substituted in the 4-position by halogen, methyl, trifluoromethyl or ethoxy.

7. A compound according to claim 1 which is 3-(4-ethoxyphenyl)-3-[3-(3-phenoxyphenyl)propyl]oxetane, 3-(4-ethoxyphenyl)-3-[3-(3-phenoxyphenyl)propyl]thietane or 3-(4-ethoxyphenyl)-3-(4-fluoro-3-phenoxybenzyloxymethyl)-oxetane.

8. An insecticidal or acaricidal composition which comprises an insecticidal or acaricidal effective amount of a compound according to claim 1, in admixture with conventional additives or carriers.

9. A composition according to claim 8 containing 10–90% by weight of said compound.

10. A composition according to claim 8 in which $R_4$ is 3-phenoxyphenyl or 4-fluoro-3-phenoxyphenyl.

11. A composition according to claim 10 in which A is O and B is $CH_2$.

12. A composition according to claim 11 in which $R_1$ is phenyl substituted in the 4 position by halogen, methyl, trifluoromethyl or ethoxy.

13. A composition according to claim 8 in which said compound is is 3-(4-ethoxyphenyl)-3-[3-(3-phenoxyphenyl)propyl]oxetane, 3-(4-ethoxyphenyl)-3-[3-(3-phenoxyphenyl)propyl]thietane or 3-(4-ethoxyphenyl)-3-(4-fluoro-3-phenoxybenzyloxymethyl)-oxetane.

14. A method of combatting insects or acarids which comprises applying to the insect, acarid or their locus, an effective insecticidal or acaricidal amount of a compound according to claim 1.

15. A method according to claim 14 in which $R_4$ is 3-phenoxyphenyl or 4-fluoro-3-phenoxyphenyl.

16. A method according to claim 15 in which A is O and B is $CH_2$.

17. A method according to claim 16 in which $R_1$ is phenyl substituted in the 4 position by halogen, methyl, trifluoromethyl or ethoxy.

18. A method according to claim 14 in which said compound is 3-(4-ethoxyphenyl)-3-[3-(3-phenoxyphenyl)propyl]oxetane, 3-(4-ethoxyphenyl)-3-[3-(3-phenoxyphenyl)propyl]thietane or 3-(4-ethoxyphenyl)-3-(4-fluoro-3-phenoxybenzyloxymethyl)-oxetane.

* * * * *